US006873866B2

(12) United States Patent
Briandet et al.

(10) Patent No.: US 6,873,866 B2
(45) Date of Patent: Mar. 29, 2005

(54) STEREOSCOPIC VISUALIZATION OF BEATING HEART

(75) Inventors: Philippe Briandet, Ellicott City, MD (US); Bogdan Chitimus, Columbia, MD (US)

(73) Assignee: Segami Corporation, Columbia, MD (US)

( * ) Notice: Subject to any disclaimer, the term of this patent is extended or adjusted under 35 U.S.C. 154(b) by 55 days.

(21) Appl. No.: 10/454,464

(22) Filed: Jun. 4, 2003

(65) Prior Publication Data

US 2004/0249273 A1  Dec. 9, 2004

(51) Int. Cl.[7] ............................................... A61B 5/00
(52) U.S. Cl. .................................................... 600/407
(58) Field of Search ........................ 600/443, 415, 600/437, 450, 407, 409, 508; 378/98.2, 41, 378/42, 29, 190, 210

(56) References Cited

U.S. PATENT DOCUMENTS

| 4,181,839 A | | 1/1980 | Hatton et al. | |
| 5,054,045 A | * | 10/1991 | Whiting et al. | 378/98.2 |
| 5,233,639 A | * | 8/1993 | Marks | 378/42 |
| 5,435,310 A | * | 7/1995 | Sheehan et al. | 600/416 |
| 5,457,728 A | * | 10/1995 | Whiting et al. | 378/98.2 |
| 5,503,152 A | | 4/1996 | Oakley et al. | |
| 5,586,201 A | * | 12/1996 | Whiting et al. | 378/98.2 |
| 5,601,084 A | | 2/1997 | Sheehan et al. | |
| 5,687,737 A | | 11/1997 | Branham et al. | |
| 5,730,129 A | | 3/1998 | Darrow et al. | |
| 5,822,391 A | * | 10/1998 | Whiting et al. | 378/98.2 |
| 6,027,451 A | | 2/2000 | McGee et al. | |
| 6,181,768 B1 | * | 1/2001 | Berliner | 378/41 |
| 6,398,736 B1 | | 6/2002 | Seward | |
| 2002/0101658 A1 | * | 8/2002 | Hoppenstein et al. | 359/466 |
| 2003/0065020 A1 | * | 4/2003 | Gale et al. | 514/423 |
| 2003/0078500 A1 | * | 4/2003 | Evron et al. | 600/443 |

OTHER PUBLICATIONS

Lorenz, Christine H., Pastorek, John S., Bundy, Feffrey M. Delineation of normal human left ventricular twist throughout systole, tagged cine magnetic resonance imaging. Journal of Cardiovascular Magnetic Resonance, vol. 2, Issue 2, 2000, pp. 97-108.

* cited by examiner

Primary Examiner—Francis J. Jaworski
(74) Attorney, Agent, or Firm—William S. Ramsey

(57) ABSTRACT

This process substantially reduces the time and effort required in analysis of recorded cardioangiograms. This process takes advantage of cardiac twist, the slight rotation of the heart about a vertical axis when the heart beats. A frame near or at the beginning of cardiac twist is selected and a second frame later on in the twist is also selected. Selection of the frames can be manual or automatic. The frames are viewed by conventional stereoscopic methods. The positions of the coronary arteries with respect to the heart are clearly shown in the three dimensional visualization.

19 Claims, 2 Drawing Sheets

STEREOSCOPIC VISUALIZATION OF BEATING HEART

CROSS-REFERENCE TO RELATED APPLICATIONS

Not applicable.

STATEMENT REGARDING FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

This invention relates to methods for visualization of the coronary arteries which supply blood to the heart.

2. Description of Related Art Including Information Disclosed Under 37 CFR 1.97 and 37 CFR 1.98.

The arteries which supply blood to the heart itself are termed "coronary" because they encircle the heart like a crown. These arteries handle 5% of the blood flow in the body and coronary artery disease is a leading cause of death. The arteries which encircle the heart have extensive bifurcation or branching and supply blood to every portion of the heart. This mass of interwoven arteries has been described as forming a labyrinth web or as resembling the roots of a tree. Therapeutic intervention in coronary artery disease, however, may require unambiguous identification of the coronary arteries. This task is complicated by the fact that the angiograms, which allow visualization of the arteries, portray them in stark contrast while the heart itself appears indistinct and shadowy. This patent application discloses a method of analysis of angiograms, applicable to recorded or real time angiograms, which facilitates unambiguous identification of the coronary arteries.

In particular, the slight rotation of the heart (twist) which accompanies a heartbeat is exploited to provide the angular offset of two images which allows the generation of a stereoscopic view using a single, non-moving image collector. Use of this process in connection with conventional angiograms allows examination of the coronary arteries and definitive determination of the position of each artery with respect to the heart, particularly which arteries are in front and which are behind the myocardium Use of this method results in substantial reduction of time required to correctly interpret coronary angiograms.

A study of the movements of the beating human hearts of 10 healthy volunteers has provided details of this phenomenon, termed "cardiac twist". During isovolumetric contraction, all ventricular twist was counterclockwise. Later in systole, the basal segments changed direction and rotated in a clockwise direction, whereas the apical segments continued counterclockwise rotation. The mean short axis net ventricular twist (apex-base) at 80% systole was 12.6±1.5 degrees. The four wall segments were heterogeneous in twist with lateral wall at 20.6±1.7 degrees; anterior wall, 17.5±5.1 degrees; inferior wall, 8.8±1.5 degrees, septum 3.5±2.4 degrees. The twist between anterior and lateral walls was significantly different from the other walls. It was concluded that twist was a robust parameter of myocardial function. Lorenz, C. H., Pastorek, J. S., and Bundy, J. M. Delineation of Normal Human Left Ventricular Twist Throughout Systole Tagged Cine Magnetic Resonance Imaging. Journal of Cardiovascular Magnetic Resonance, Vol. 2, issue 2 (2000), pp. 97-98.

Current angiogram examination of patients involves the injection of an x-ray opaque dye into an artery, followed by the recording of an x-ray angiogram which shows the arteries in stark contrast. A recorded angiogram is similar to a motion picture with individual pictures or frames taken at from 10 to 100 frames per second. The procedure involves repeated injections and recording after slight repositioning of the detector between injections. This is because of the need to unambiguously identify arteries despite the fact that a single angiogram does not allow distinguishing between arteries on the front and the back of the heart. By recording repeated angiograms from different angles, the coronary arteries can be identified. The process, however, involves intensive study of recorded angiograms by skilled specialists and the study of one set of angiograms may require several specialists and one half hour of time.

Stereoscopic three-dimension images are a mental construct created by the essentially simultaneous viewing of separate images of a three-dimensional object by the left and right eyes. The separate images of the same scene differ by an angular offset which corresponds to the fact that the viewer's eyes are offset horizontally. This offset, also termed "binocular disparity" corresponds to the slightly different views of a three-dimension object seen by the left and right eyes. In this invention cardiac twist is used to provide the offset which allows the stereoscopic viewing of cardiogram images and facilitates the identification of cardiac arteries.

U.S. Pat. No. 4,181,839 discloses a collimator which simultaneously provides two separate views of an internal organ, especially a heart. Images are created by the radioactive decay of injected labeled materials which are detected by an Anger or fluoroscope scintillation camera. The offset required for stereoscopic images are obtained by taking views at two different angles, such as 45° and 135° or 60° and 120° etc. and there is no need to move camera or patient. The views may be used to provide multiple images for stereoscopic three-dimension views of an organ.

U.S. Pat. No. 5,233,639 discloses a stereoscopic fluoroscope and method of producing stereoscopic X-ray images. This involves an X-ray source and image intensifies which are rotated at the same angular velocity in order to obtain the offset required for the stereoscopic viewing.

U.S. Pat. No. 5,503,152 discloses an ultrasonic transducer with parallel arrays of transducer elements used to simultaneously view an organ, the spacing of the multiple elements used to provide the offset required for a stereoscopic display.

U.S. Pat. No. 5,601,084 discloses an ultrasonic imaging data transesophageal probe which images the end of the systole and end of the diastole portions of the cardiac cycle. The data are analyzed and provide information on the pumping volume and thickness of cardiac wall. The probe is used to obtain a variety of displaced images. The offset required for stereoscopic viewing is obtained by moving the probe with respect to the heart.

U.S. Pat. No. 5,687,737 discloses an electrophysiological mapping system which covers the external or internal surface of the heart with an array of electrodes. A sock with attached electrodes is stretched over the outside of the heart or a balloon with attached electrodes is inserted into a ventricular cavity and inflated. The data are displayed on a three-dimension image which is generated by a program which integrates the multi-electrode data and generates an image. The generated image is not a stereoscopic image.

U.S. Pat. No. 5,730,129 discloses a device with an internal probe whose position is monitored by magnetic resonance or through radio-frequency. The internal probe is inserted into a body cavity and an external ultrasonic probe which is attached to the outer surface of the patient. The use of the external probe allows the operator to orient the location of the internal probe despite movement of the organ or of the patient.

U.S. Pat. No. 6,027,451 discloses an apparatus with a first ultrasonic transducer attached to a catheter and attached to a data processing device and a second ultrasonic transducer which is attached to the external surface of the body. This allows orientation of the image from the first transducer despite rotation of the transducer on insertion and despite movement of the heart and the lungs.

U.S. Pat. No. 6,398,736 discloses an ultrasonic catheter for insertion into the large vessels of the heart. Images are displayed in which collects images in 2d, 3d, 4d and higher dimensions through parametric expression of flow. Doppler ultrasound displays blood flow in three-dimension images which are not stereoscopic images.

The discovered prior art inventions do not disclose the present invention. In particular, the prior art methods involve acquiring stereoscopic displacement or offset through relative movement of a single detector, or through the use of multiple detectors. The present invention exploits the natural slight rotational movement about the vertical axis of the heart associated with the heartbeat to provide the stereoscopic displacement necessary for stereoscopic visualization. Such stereoscopic visualization facilitates unambiguous determination of the identity and location of coronary arteries.

BRIEF SUMMARY OF THE INVENTION

This patent application discloses a method of stereoscopic visualization of coronary arteries in recorded angiograms in which at least one cardiac cycle is recorded. A first frame is selected, and a second frame is selected which had been recorded after cardiac twist provided sufficient offset to allow stereoscopic viewing of the first and second frames. The pair of first and second frames is viewed wherein the first frame is viewed with one of the viewer's eyes only, and the second frame is viewed by the viewer's other eye only.

The objective of this disclosure is to provide a method for stereoscopic viewing of recorded angiograms.

Another objective of this disclosure is to provide for the unambiguous identification of coronary arteries in recorded angiograms.

Another objective of this disclosure is to reduce the time required for examination of recorded angiograms.

Another objective of this disclosure is to reduce the number of injection of dye required for an angiogram procedure.

Another objective of this disclosure is to facilitate medical therapy based on recorded angiograms.

A final objective of this disclosure is to provide stereoscopic viewing of coronary arteries using means which are quick, inexpensive, and without harmful effects on patients or the environment.

DETAILED DESCRIPTION OF THE INVENTION

Figure 1:
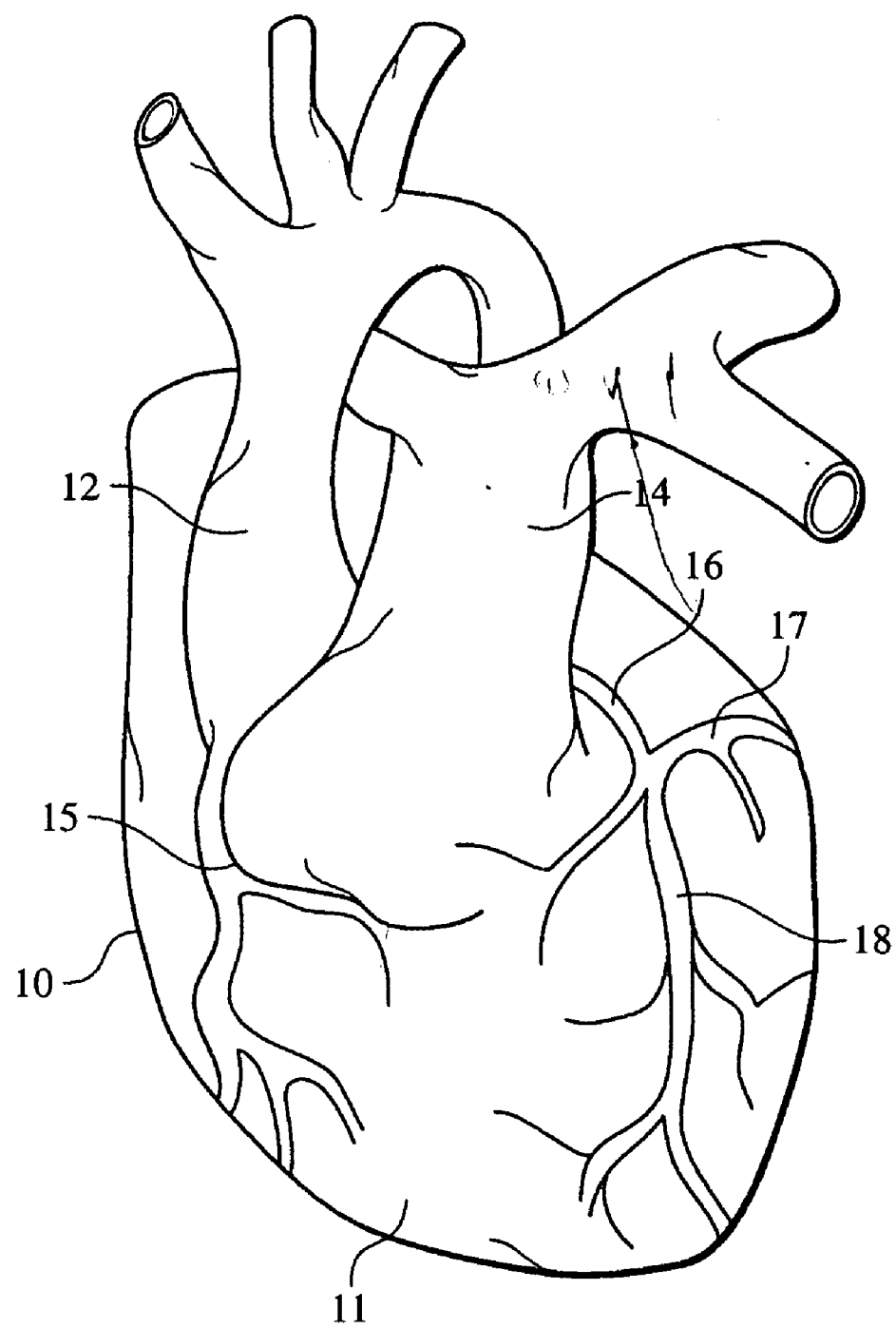
FIG. 1 is a diagrammatic representation of the front of the heart showing blood vessels.

In this patent application the term "visualization" refers to methods of obtaining graphic images of organs by any means, including X-ray, and scintigraphy. The preferred embodiment is in application to X-ray cardioangiograms using non-toxic, injectable, radiopaque substances to make visible the coronary arteries.

The term "stereoscopic pair" means two single images in which the images of the object are sufficiently angularly displaced or offset to allow a three-dimensional effect when viewed in a stereoscopic view under conditions where one image is viewed with the left eye and a second offset image is viewed essentially simultaneously with the right eye. This displacement of images is also termed "binocular disparity". The term "stereoscopic view" refers to any means of viewing a stereoscopic pair which involves generation of a three-dimension effect in the viewer. This including viewing of paper images using devices which allow each eye to view one of a stereoscopic pair, and viewing images printed using two colors which are viewed using glasses with differently colored lenses.

Preferably an electronic display is used in which stereoscopic pair images are displayed sequentially and are viewed using glasses which become sequentially transparent and opaque so that the image destined to be viewed by the left eye is viewed when the glass covering the left eye is transparent and the glass covering the right eye is opaque. The image destined to be viewed by the right eye is viewed when the glass covering the right eye is transparent and the glass covering the left eye is opaque. The sequential viewing of such images provides the stereoscopic view or stereoscopic effect.

Another preferred electronic display uses a flat panel display in which the left and right halves of stereoscopic pairs are displayed on alternative columns of pixels on the liquid crystal display. Both half of the pairs are displayed simultaneously and the observer located directly before the display observes the stereoscopic pairs with a stereoscopic effect.

Other means of observing the stereoscopic pairs involve displaying the pairs on a plasma screen, on film, or projected onto a screen.

In operation of the methods of this invention, conventional cardioangiograms are produced and recorded using, for example, the INFINIX CS cardiac and vascular system. INFINIX CS is a trademark for an x-ray system obtainable from Toshiba America Medical Systems, Inc., Tustin, Calif. These angiograms are typically recorded on CDs or DVDs for further analysis.

In a second embodiment, the recorded angiograms are not removed from the x-ray system but are viewed directly at the x-ray system. A suitable computer, graphics card, and a CRT or flat panel LCD display are incorporated into the x-ray system.

Any suitable personal computer can be used in generating the stereoscopic pairs from angiograms recorded on CDs or DVDs. A preferred personal computer is one which includes a WINDOWS 9X/ME/2000/XP operating system. WINDOWS 9X/ME/2000/XP are trademarks for operating systems which may be obtained from Microsoft Corporation, Redmond Wash. It is necessary that the computer have a graphics card with stereo support.

Any suitable graphics card which allows viewing of stereoscopic pairs may be used. A preferred graphics card is the QUADRO FX 2000 graphics card. QUADRO FX 2000 is a trademark for a graphics card which may be obtained from Nvidia Corporation, Santa Clara, Calif.

Stereo support in the form of viewing glasses and software allows the viewing of stereoscopic pairs displayed on a CRT. A preferred stereo support is the EXTREME 3D PC SYSTEM stereo support which includes glasses with lenses which become alternatively opaque and transparent and software. EXTREME 3D PC SYSTEM is a trademark for a stereo support which may be obtained from X3D Technologies Corp. New York, N.Y.

A flat panel LCD display also can be used for electronic viewing of stereoscopic pairs without glasses. A preferred system is the 2015XLS 3D LDC display. 2015XLS is a trademark for a display which may be obtained from Dimension Technologies Inc., Rochester, N.Y.

Cardiac twist is the slight rotation of the beating heart about an axis roughly parallel to the vertical axis of the body. The heart rotates or twists slightly in a counterclockwise direction (viewed from the head) at the beginning of the cardiac cycle. The cardiac cycle can be though of as beginning with the filling of the right atrium with blood from the superior vena cava and the inferior vena cava, contraction of the right atrium sending blood into the right ventricle, contraction of the right ventricle sending blood into the pulmonary artery, freshly oxygenated blood from the pulmonary vein entering the left atrium. Almost simultaneously with the contraction of the right atrium, the left atrium contracts, sending blood into the left ventricle which then contracts, sending blood into the aorta and throughout the body. At the end of the cardiac cycle the heart rotates or twists slightly in a clockwise direction thereby restoring the heart to the original position.

Rotation of the heart is not uniform along the long axis of the heart, causing the motion to be described as a twist, much as the wringing of a wet wash cloth. The fact which gives this invention utility, however, is that regardless of the direction and extent of the rotation at any particular point on the surface of the heart at any particular point in the beat cycle, the movement is sufficiently uniform in the area of the coronary arteries to provide a useful stereoscopic view of most of the arterial tree. This rotation or twisting motion provides the angular offset necessary for the generation of stereoscopic pairs for stereoscopic viewing.

This invention exploits the fact that cardiac twist causes enough rotation of the heart to allow the generation of stereoscopic pairs from recorded cardioangiograms. Images of a single beat are used. It is not necessary that sequential frames from a recorded sequence be used. Rather it is important that frames from a sequence are selected which in which images of the twisting heart are displaced through rotation enough in time to allow a stereoscopic effect when viewed, but close enough in time that the normal contraction of the heart does not significantly alter the position of the artery.

Angiograms conventionally are recorded at a rate of 30 frames/second, although other frame rates may be used, from 10-100 frames/second. The normal resting heartbeat is approximately 65 to 75 beats/minute, with beat rates in excess of 100 beats/minute in cases of tachycardia, and beat rates of less than 50 beats/minute in cases of bradycardia. An average cardiac cycle therefore will take from 800 to 920 milliseconds; with extremes ranging from 600 to 1,200 milliseconds.

It has been found that suitable stereoscopic pairs were derived from cardioangiograms recorded with a frame rate of 33 milliseconds when frames were selected at intervals between frames of 33 to 66 milliseconds. Use of other frame rates showed that suitable pairs were derived at intervals between frames of 10 to 100 milliseconds. The choice of frames for stereoscopic pairs depends on the frame rate. Enough cardiac twist must occur between the selected frames to provide suitable angular offset. Excessive time between selected frames, however, may cause undesirable displacement of arteries by cardiac contraction. Sequential and every other frames have proven suitable stereoscopic pairs, depending on frame rate. Use of a relatively rapid frame rate results in suitable stereoscopic pairs with a greater number of frames between the selected frames. Selection of frames can be done manually or automatically.

Since cardiac twist over one cardiac cycle has been found to be approximately 12°, stereoscopic pairs taken at intervals of 33 and 66 milliseconds correspond to a twist between selected frames of approximately 1.5° and 3°, respectively assuming the rate of twist is approximately constant over the cardiac cycle and the twist is reversed in direction at the start of the diastole or filling phase of the cardiac cycle. An interval of 10 to 100 milliseconds between selected frames would involve cardiac twist of approximately 0.5° to 5°.

Recorded angiograms covering several of the cardiac cycles or beats have been used. The order of the sequential frames used as stereoscopic pairs is reversed when the twist of the heart reverses directions. For example, in a series of sequential recorded frames, suitable stereoscopic pairs during the initial counterclockwise twist might be 1-2, 2-3, 3-4, 4-5, 5-6, 6-7, 7-8, 8-9, 9-10, 10-11, and 11-12. During the clockwise reversal of the twist the suitable stereoscopic pairs would be 14-13, 15-14, 16-15, 17-16, 18-17, 19-18, 20-19, 21-20, 22-21, and 23-22. The first frame in the pair would be viewed by the right eye and the second frame by the left eye FIG. 1 is a diagrammatic representation of the heart 10 showing blood vessels. Visible in FIG. 1 is the myocardium 11 or heart muscle. Also visible in FIG. 1 is the aorta 12 and pulmonary artery 14. The right coronary artery 15 is shown, as is the left main coronary artery 16, the circumflex coronary artery 17, and the left anterior descending coronary artery 18.

Figure 2:
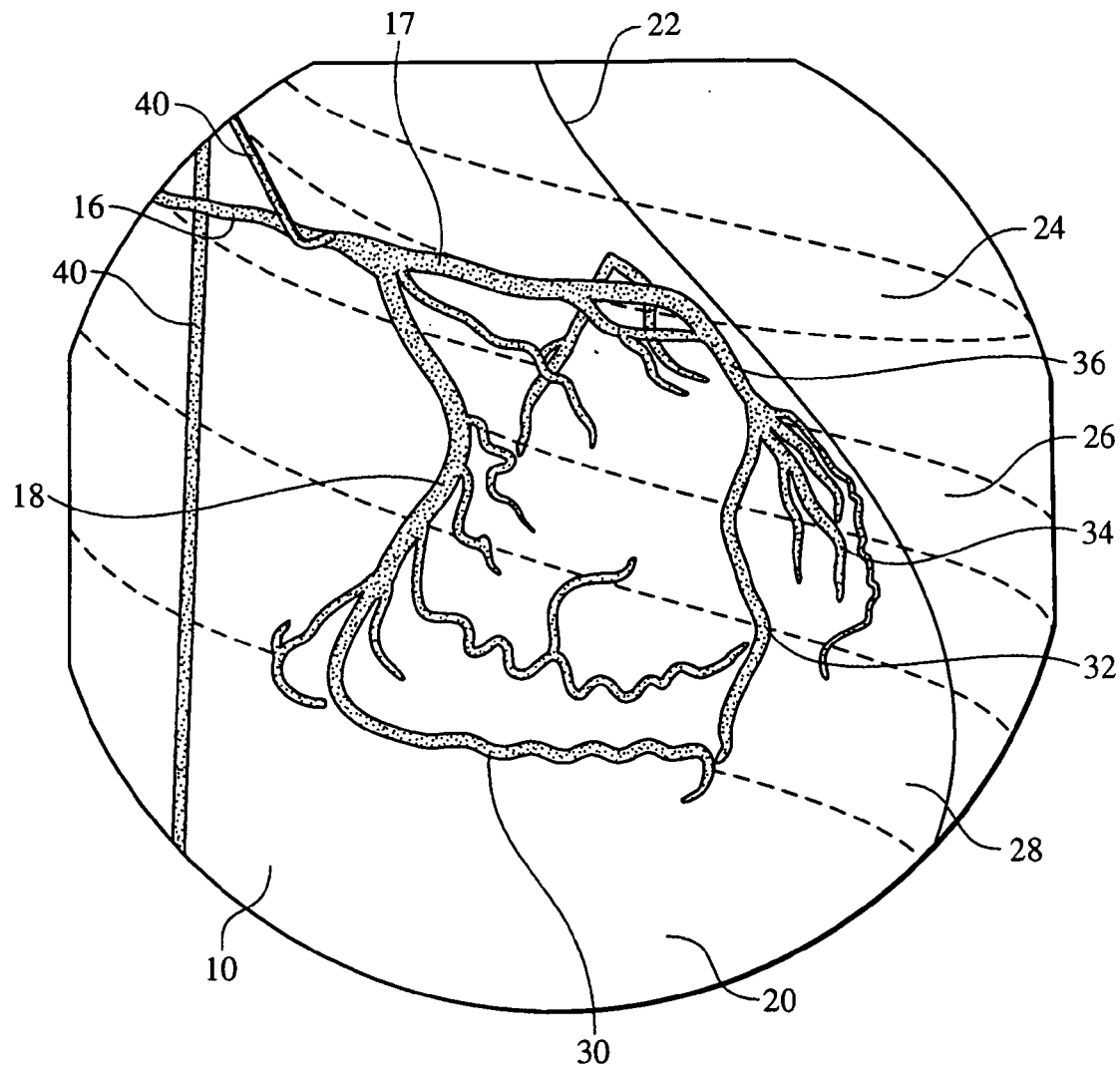
FIG. 2 is a tracing of a frame of an angiogram showing normal coronary arteries surrounding the left ventricle.

FIG. 2 is a tracing of one frame of an angiogram of the heart in which some of the coronary arteries had been filled with a dye which made those vessels relatively opaque to x-rays. In such angiograms the heart itself is faintly visible as a shadow. FIG. 2 shows a portion of the left auricle 20 of the heart 10 and includes the left edge 22 of the heart. Also visible in FIG. 2 are portions of three ribs, 24, 26, 28, depicted by dotted lines. A catheter 40 which delivered dye to the left main coronary artery 16 is visible along the left margin and at the top of FIG. 2. The circumflex coronary artery 17 and left anterior descending coronary 18 are visible in FIG. 2. A large number of branched arteries 30, 32, 34, 36 are visible in FIG. 2. It is impossible to determine the location of the visible branched arteries with respect to the surface of the heart from examination of the angiogram depicted in FIG. 2. However, the use of the methods of this invention allowed the unambiguous determination of their location. Arteries 16, 17, 18, 30 and 32 were on the front or proximal surface of the left ventricle 20. Artery 36 was on the left side of the ventricle. Artery 34 was on the back or distal surface of the left ventricle.

FIG. 2 illustrates the difficulties in interpretation of angiograms which are relieved by the methods of this invention. The coronary arteries often do not appear in predictable locations on the heart, but due to disease, genetic variation, or primary individual variation the arteries appear in a wide variation of places. Since coronary arteries encircle the heart, it is often difficult to determine if a specific artery or portion of an artery is at the front side or the back side of the heart because the angiogram depicts the arteries in stark contrast but depicts the myocardium only in faint shadow. The methods of the present invention provide a stereoscopic view of the arteries which allows rapid unambiguous location of the arteries and of diseased portions of the arteries. This facilitates therapy for the diseased portions, by means of angioplasty, insertion of a stent or bypass surgery.

It will be apparent to those skilled in the art that the examples and embodiments described herein are by way of illustration and not of limitation, and that other examples may be used without departing from the spirit and scope of the present invention, as set forth in the appended claims.

We claim:

1. The method of stereoscopic visualization of coronary arteries and of myocardium in a beating heart in recorded angiograms in which at least one cardiac cycle is recorded comprising the steps:
   a. selecting a first frame,
   b. selecting a second frame recorded after cardiac twist provided approximately 0.5° to 5° rotation of the heart, and
   c. viewing the first and second frames wherein the first frame is viewed by one of the viewer's eyes only and the second frame is viewed by the viewer's other eye only.

2. The method of claim 1 further comprising the step after steps c.:
   d. identifying the location of the coronary arteries with respect to the myocardium.

3. The method of claim 1 wherein the second frame is recorded from 10 to 100 milliseconds after the first frame.

4. The method of claim 1 wherein the second frame is recorded from 33 to 66 milliseconds after the first frame.

5. The method of claim 1 wherein the first and second frames are next in sequence.

6. The method of claim 1 wherein the first and second frames are separated by one or more frames in the recorded angiogram.

7. The method of claim 1 wherein the recorded angiogram comprises frames recorded from several of the cardiac cycles.

8. The method of claim 1 wherein the recorded angiogram is recorded on a CD or DVD.

9. The method of claim 1 wherein the cardiac twist between selected frames is approximately 1.5° to 3.0°.

10. The method of claim 1 wherein the selected frames are viewed as paper images.

11. The method of claim 1 wherein the selected frames are viewed as electronic images.

12. The method of claim 11 wherein the selected frames are viewed displayed on a CRT display.

13. The method of claim 11 wherein the selected frames are viewed displayed on a LCD monitor.

14. The method of claim 11 wherein the selected frames are viewed displayed on a plasma screen.

15. The method of claim 1 wherein the selected frames are viewed displayed on film.

16. The method of claim 1 wherein the selected frames are viewed displayed as projected images.

17. The method of claim 1 wherein the selected frames are viewed on a stereoscopic display incorporated in an x-ray system.

18. The method of identifying coronary arteries and myocardium in a beating heart which requires only a single injection of an x-ray opaque dye into an artery comprising the steps:
   a. injecting an x-ray opaque dye into an artery,
   b. recording an angiogram over sufficient time for cardiac twist to rotate the heart approximately 0.5° to 5°,
   c. selecting a first frame,
   d. selecting a second frame recorded after cardiac twist rotated the heart approximately 0.50 to 5°, and
   e. viewing the first and second frames wherein the first frame is viewed by one of the viewer's eyes only and the second frame is viewed by the viewer's other eye only.

19. The method of claim 18 further comprising the step after step e.:
   f. identifying the location of the coronary arteries with respect to the myocardium.

* * * * *